US007138256B2

(12) United States Patent
Zander et al.

(10) Patent No.: US 7,138,256 B2
(45) Date of Patent: Nov. 21, 2006

(54) PROCESSES FOR PREPARING CONJUGATED LINOLEIC ACID FROM CONJUGATED LINOLEIC ACID ESTERS

(75) Inventors: Lars Zander, Duesseldorf (DE); Stefan Busch, Oberhausen (DE); Carolin Meyer, Duesseldorf (DE); Sabine Both, Duesseldorf (DE); Ulrich Schoerken, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/516,987

(22) PCT Filed: May 28, 2003

(86) PCT No.: PCT/EP03/05598

§ 371 (c)(1),
(2), (4) Date: Dec. 6, 2004

(87) PCT Pub. No.: WO03/104472

PCT Pub. Date: Dec. 18, 2003

(65) Prior Publication Data

US 2005/0255570 A1    Nov. 17, 2005

(30) Foreign Application Priority Data

Jun. 6, 2002   (DE) ............................... 102 25 117

(51) Int. Cl.
*C12P 7/64* (2006.01)
(52) U.S. Cl. ...................... 435/134; 554/126; 554/223; 554/224

(58) Field of Classification Search ................ 554/126, 554/223, 224; 435/134
See application file for complete search history.

(56) References Cited

U.S. PATENT DOCUMENTS 6,184,009 B1 * 2/2001 Cain et al. .................. 435/134
6,316,645 B1 * 11/2001 Sih et al. .................... 554/126

FOREIGN PATENT DOCUMENTS

EP    1 097 708 A1    5/2001

OTHER PUBLICATIONS

McNeill G P et al: "Enzymatic Enrichment of Conjugated Linoleic acid Isomers and Incorporation into Triglycerides" Journal of the American Oil Chemists' Society, American Oil Chemists' Society, Champaign, US, vol. 76, No. 11, Nov. 1999, pp. 1265-1628, XP001026473.
Haas M J et al: "Lipase-Catalyzed Fractionation of Conjugated Linoleic Acid Isomers" Lipids, Champaign, IL, US, vol. 34, No. 9, Sep. 1999, pp. 979-987, XP001056347 ISSN: 0024-4201.

\* cited by examiner

*Primary Examiner*—Deborah D. Carr
(74) *Attorney, Agent, or Firm*—John F. Daniels

(57) ABSTRACT

Processes for preparing conjugated linoleic acid are described wherein a conjugated linoleic acid lower alkyl ester is subjected to hydrolysis in the presence of an enzyme to form a hydrolyzate comprising a conjugated linoleic acid and a lower alkanol, wherein at least a portion of the lower alkanol is continuously removed; the hydrolyzate is separated into an organic phase and an aqueous/alcoholic phase; and the conjugated linoleic acid is separated from the organic phase.

17 Claims, No Drawings

PROCESSES FOR PREPARING CONJUGATED LINOLEIC ACID FROM CONJUGATED LINOLEIC ACID ESTERS

BACKGROUND OF THE INVENTION

1. Field of the Invention

This invention relates generally to fatty acids and, more particularly, to a new process for the production of conjugated linoleic acid by enzymatic hydrolysis of its esters.

2. Prior Art

Linoleic acids with conjugated double bonds, which are commercially available as "CLA" (conjugated linoleic acids), are physiologically active and are used as food additives. Conjugated linoleic acid is normally produced from triglycerides which have a high percentage content of—normally unconjugated—linoleic acid, such as thistle or sunflower oil for example. The triglycerides are isomerized in the presence of basic catalysts or enzymes and then saponified. A disadvantage in this regard is that, on the one hand, the saponification step yields many unwanted waste materials and, on the other hand, large quantities of alkalis are required, which can quickly result in corrosion in the reactors used. To avoid this, linoleic acid alkyl esters have more recently been used as preferred starting materials and, in a first step, are isomerized to the CLA esters and then saponified. However, even this process is not entirely convincing because it is also attended by disadvantages, such as for example poor yields, drastic reaction conditions, unwanted secondary products and long reaction times.

Accordingly, the problem addressed by the present invention was to provide a process for the production of conjugated linoleic acid which would reliably avoid the abovementioned disadvantages of the prior art.

BRIEF SUMMARY OF THE INVENTION

The present invention relates, in general, to fatty acids and, more particularly, to new processes for the production of conjugated linoleic acid by enzymatic hydrolysis of conjugated linoleic acid esters.

The present invention relates to a process for the production of conjugated linoleic acid, in which (a) conjugated linoleic acid lower alkyl esters are hydrolyzed with water in the presence of enzymes with continuous removal of alcohol, (b) the hydrolyzate is separated into an organic phase and an aqueous/alcoholic phase and (c) the organic phase containing the conjugated linoleic acid is freed from unreacted conjugated linoleic acid lower alkyl esters.

It has surprisingly been found that enzymatic hydrolysis with continuous removal of alcohol leads to fatty acids that are free from unwanted secondary products. High yields are obtained, the process involves mild reaction conditions and uses catalysts which meet all environmental compatibility requirements. In addition, if alcohol is removed continuously from the hydrolysis reactor itself during the hydrolysis process, a much faster conversion is achieved in a one-step process.

DETAILED DESCRIPTION OF THE INVENTION

Conjugated Linoleic Acid Lower Alkyl Esters

Starting materials for the process according to the invention are linoleic acid lower alkyl esters which preferably correspond to formula (I):

$$R^1CO\text{—}OR^2 \qquad (I)$$

where $R^1CO$ is the acyl group of a linoleic acid containing conjugated double bonds and $R^2$ is a linear or branched alkyl group containing 1 to 4 carbon atoms. In one particular embodiment, conjugated linoleic acid methyl and/or ethyl esters are used.

Enzymes

Typical—but not limiting—examples of suitable enzymes are lipases and/or esterases of microorganisms selected from the group consisting of *Alcaligenes* sp., *Aspergillus niger*, *Candida antarctica* A, *Candida antarctica* B, *Candida cylindracea*, *Chromobacterium viscosum*, *Rhizomucor miehei*, *Penicilium camemberti*, *Penicilium roqueforti*, *Porcine pancreas*, *Pseudomonas cepacia*, *Pseudomonas fluorescens*, *Rhizopus javanicus*, *Rhizopus oryzae*, *Thermomyces lanugenosus* and mixtures thereof. Lipases and esterases from the organisms *Alcaligenes, Candida, Chromobacterium, Rhizomucor, Pseudomonas, Rhizopus* and *Thermomyces* are preferred because they are particularly active. The enzymes are generally used in the form of dilute suspensions or water-based concentrates. The lipases/esterases may also be immobilized on carrier material and re-used in so-called repeated batches.

Hydrolysis

The hydrolysis of the fatty acid alkyl esters is preferably carried out at mild temperatures in the range from 20 to 80° C., preferably in the range from 30 to 70° C. and more particularly in the range from 35 to 60° C. with continuous removal of the lower alcohol, i.e. normally methanol or ethanol, under reduced pressure, the preferred temperature being determined by the activity optimum of the enzymes used.

A) A suitable hydrolysis process is a batch process in which a constant water content—normally between 30 and 70% by weight—is maintained in the reactor by subsequent additions of water. The reaction is normally carried out at a temperature of 30 to 50° C. and under a reduced pressure of 20 to 60±5 mbar. In this batch process, an alcohol/water mixture is continuously removed ("stripped").

B) Another suitable hydrolysis process is a batch process in which water is continuously introduced and an alcohol/water mixture is continuously removed ("stripped"). The water content in the reactor in this process is usually low (0 to 20% by weight). The reaction is normally carried out at a temperature of 50 to 70° C. and under a reduced pressure of 20 to 60±5 mbar.

C) An alternative, but equally suitable, hydrolysis process is a multistage process without continuous removal of the alcohol component. On termination of the enzymatic hydrolysis, the water phase, which also contains large parts of the water-soluble short-chain alcohol, is separated from the organic phase and a fresh water phase is added. Typically, the water phase is changed 1 to 3 times. The reaction is normally carried out at a temperature of 20 to 70° C. and at a water content of 50 to 75%. The hydrolysis may be carried out with immobilized enzyme, which may be re-used in each hydrolysis stage, and with non-immobilized enzyme. In that case, fresh enzymes has to be added in each hydrolysis stage.

Working Up

After the hydrolysis, the water/alcohol phase is separated from the organic phase which is worked up, i.e. unreacted alkyl ester is removed from the valuable product. Different conversion rates are obtained according to the duration of the hydrolysis. The reaction may be terminated early, for example at a conversion of only. 60% by weight, so that fatty acids and fatty acid esters have to be subsequently separated. However, it may also be terminated at a conversion of >90% by weight, preferably >95% by weight or even >99% by weight, so that subsequent separation is unnecessary. Separation may be carried out by distillation or by saponification of the free fatty acid and subsequent phase separation. However, complete hydrolysis of the conjugated linoleic acid esters (conversion >99%) under mild reaction conditions is particularly preferred in order to avoid changes in the isomer composition.

EXAMPLES

Example 1

Selection of Suitable Lipases.

15 Batches each containing 4 g conjugated linoleic acid ethyl ester and 6 g water in a closable reaction vessel were simultaneously stirred at room temperature on a multi-stirrer plate. Quantities of 40 mg of commercially available lipases or esterases were added to the batches. Samples are taken after reaction times of 2 h and 22 h. The organic phase containing fatty acid ethyl ester and enzymatically hydrolyzed fatty acid were separated and analyzed. The conversion was determined via the acid value. The results are set out in Table 1.

All the lipases and esterases tested were found to be active in the hydrolysis of the fatty acid esters. However, microorganisms of the *Alcaligenes, Candida, Chromobacterium, Penicilium, Pseudomonas, Rhizopus* and *Thermomyces* type are preferred. The reaction without removal of ethanol under the above conditions continued to an equilibrium of ca. 30% by weight free fatty acid.

Example 2

Hydrolysis of Short-chain Conjugated Linoleic Acid Methyl Esters with Continuous Stripping of Water and Methanol Hydrolysis Test using Process A)

400 g conjugated linoleic acid methyl ester, 200 g water and 20 g *Candida antarctica* B lipase immobilized on polypropylene were introduced into a heatable flask. The reaction was carried out with a distillation bridge surmounting the flask under a reduced pressure of 60 mbar and at a temperature of 60° C. Water was continuously pumped into the flask at a flow rate of 0.5 ml/min. and a water content of 30 to 40% was adjusted in the flask. The conversion of the reaction was determined via the acid value. On termination of the reaction, the reaction mixture was filtered off from the immobilized enzyme and the organic phase was separated from the aqueous phase. An acid value of 200 corresponded to a 100% conversion. The results are set out in Table 2.

TABLE 2

Conversion after different reaction times with stripping of water and methanol

| Reaction time [h] | Acid value | Conversion [%] |
|---|---|---|
| 0 | 0 | 0 |
| 2 | 96.4 | 48.2 |
| 8 | 139.2 | 69.6 |
| 24 | 189.5 | 94.7 |
| 48 | 198.8 | 99.4 |

TABLE 1

Lipases and esterases used

| | | | Acid value | | Conversion | |
|---|---|---|---|---|---|---|
| Enzyme | Microorganism | Manufacturer | 2 h | 22 h | 2 h | 22 h |
| Chirazym L-10 | *Alcaligenes* sp. | Roche | 21 | 41 | 11.5 | 20.5 |
| Lipase A | *Aspergillus niger* | Amano | 6 | 16 | 3 | 8 |
| Novozym 868 | *Candida antarctica* A | Novozymes | 5 | 6 | 2.5 | 3 |
| Novozym 525 | *Candida antarctica* B | Novozymes | 52 | 62 | 26 | 30 |
| Lipomod 34 | *Candida cylindracea* | Biocatalysts | 45 | 61 | 22.5 | 30 |
| Lipase LP | *Chromobacterium viscosum* | Asahi Kasei | 45 | 60 | 22.5 | 30 |
| Novozym 388 | *Rhizomucor meihei* | Novozymes | 8 | 11 | 4 | 5.5 |
| Lipase G | *Penicilium camemberti* | Amano | 15 | 38 | 7.5 | 19 |
| Lipase R | *Penicilium roqueforti* | Amano | 6 | 6 | 3 | 3 |
| Lipase L115P | *Porcine pancreas* | Biocatalysts | 6 | 6 | 3 | 3 |
| Lipase PS | *Pseudomonas cepacia* | Amano | 46 | 57 | 23 | 28.5 |
| Lipase AK | *Pseudomonas fluorescens* | Amano | 26 | 53 | 13 | 26.5 |
| Lipomod 36 P | *Rhizopus javanicus* | Biocatalysts | 21 | 38 | 11.5 | 19 |
| Lipase F-AP 15 | *Rhizopus oryzae* | Amano | 12 | 18 | 6 | 9 |
| Lipolase T1 100 | *Thermomyces lanugenosus* | Novozymes | 38 | 53 | 19 | 26.5 |

According to analysis of the acid value, a conjugated linoleic acid in the form of a clear, pale yellowish colored liquid was obtained with a conversion of >99% after a reaction time of 48 hours.

The isomer pattern of the enzymatically hydrolyzed CLA was compared with the starting substrate CLA methyl ester by gas chromatographic analysis.

TABLE 3

Comparison of the isomer pattern after enzymatic hydrolysis

| Analysis | CLA Me, crude | CLA FFA, crude |
|---|---|---|
| C16:0 | 3.8 | 4.3 |
| C18:0 | 2.0 | 2.4 |
| C18:1 | 16.8 | 17 |
| C18:2 | 1.9 | 2 |
| C18:2 c9, 11t | 37.5 | 37 |
| C18:2 t10, c12 | 36.8 | 36.7 |
| C18:2 cc isomers | 0.8 | 1 |
| C18:2 tt isomers | 0.5 | 0.8 |
| Acid value |  | 198.8 |

Within the limits of measurement inaccuracy, the enzymatic hydrolysis did not produce any significant change in the isomer pattern.

Example 3

Hydrolysis of Short-chain Conjugated Linoleic Acid Methyl Esters with Continuous Stripping of Water and Methanol Hydrolysis Test using Process B)

100 g conjugated linoleic acid methyl ester, 10 g water and 5 g *Candida antarctica* B lipase immobilized on polypropylene were introduced into a heatable flask. The reaction was carried out with a distillation bridge surmounting the flask under a reduced pressure of 60 mbar and at a temperature of 60° C. Water was continuously pumped into the flask at a flow rate of 0.25 ml/min. (Example 3A) and 0.5 ml/min. (Example 3B). Added water was quickly distilled off so that the water content in the reactor was low (<20%) throughout the reaction. The conversion of the reaction was determined via the acid value. The reactions were terminated after 24 h (partial conversion) and the immobilized enzyme was filtered off from the reaction mixture. The organic phase was then separated from the aqueous phase. An acid value of 200 corresponded to a 100% conversion. The results are set out in Table 4.

TABLE 4

Conversion after different reaction times with stripping of water and methanol

| Reaction time [h] | Acid value Example 3A | Conversion [%] Example 3A | Acid value Example 3B | Conversion [%] Example 3B |
|---|---|---|---|---|
| 0 | 0 | 0 | 0 | 0 |
| 2 | 51.5 | 25.7 | 62.3 | 31.1 |
| 4 | 71.2 | 35.6 | 84.4 | 42.4 |
| 6 | 87.0 | 43.5 | 100.2 | 50.1 |
| 8 | 100.0 | 50.0 | 112.2 | 56.1 |
| 24 | 153.0 | 76.5 | 167.1 | 83.5 |

Conversions of 76.5% and 83.5% were obtained after 24 h, depending on the quantity of water added. The amount of distillate in Example 3A was 315 g after 24 h and, in Example 3B, 584 g after 24 h.

Example 4

Hydrolysis of Short-chain Conjugated Linoleic Acid Ethyl Esters with Continuous Stripping of Water and Ethanol Hydrolysis Test using Process A)

100 g conjugated linoleic acid ethyl ester, 100 g water and 10 g *Thermomyces lanugenosus* lipase immobilized on polypropylene were introduced into a heatable flask. The reaction was carried out with a distillation bridge surmounting the flask under a reduced pressure of 30 mbar and at an external temperature of 60° C. Water was continuously pumped into the flask at a flow rate of 0.5 ml/min. and a water content of 40 to 60% was adjusted in the flask. The temperature inside the reactor was kept at ca. 40° C. The conversion of the reaction was determined via the acid value. On termination of the reaction, the immobilized enzyme was filtered off from the reaction mixture and the organic phase was separated from the aqueous phase. An acid value of 200 corresponded to a 100% conversion. The results are set out in Table 5.

TABLE 5

Conversion after different reaction times with stripping of water and ethanol

| Reaction time [h] | Acid value | Conversion [%] |
|---|---|---|
| 0 | 0 | 0 |
| 4 | 59.1 | 29.6 |
| 20 | 114 | 57 |
| 45 | 166 | 83 |

According to analysis of the acid value, a conjugated linoleic acid in the form of a clear, colorless liquid was obtained with a conversion of 83% after a reaction time of 45 hours.

Example 5

Hydrolysis of Short-chain Conjugated Linoleic Acid Methyl Esters by Multistage Hydrolysis Hydrolysis Test using Process C)

3 Batches each containing 20 g conjugated linoleic acid methyl ester based on the sunflower oil and 40 g water were weighed into closed flasks. Quantities of 1 g immobilized lipase were then added and the mixtures were stirred for 5 h at room temperature on a magnetic stirrer plate. The enzyme immobilizates were then filtered off and the organic phase was separated from the aqueous phase. Another 40 g water was added to the organic phase and the enzyme immobilizates filtered off were re-added to the reaction solution. After reaction overnight at room temperature, the enzyme immobilizates were again filtered off and the organic phase was separated from the aqueous phase. 40 g water was added to the organic phase and the enzyme immobilizates filtered off were re-added to the reaction solution. After another 5 h at room temperature, the reaction was terminated.

The following enzyme immobilizates were used:
5A) 1 g Novozym 435
5B) 1 g *Candida antarctica* B lipase immobilized on macroporous polypropylene The conversion of the reaction in the individual stages was determined via the acid value. An acid value of 200 corresponded to a 100% conversion. The results are set out in Table 6.

TABLE 6

Conversion in multistage hydrolysis

| Reaction time [h] | Acid value Ex. 5A | Conversion Ex. 5A | Acid value Ex. 5B | Conversion Ex. 5B | Acid value Ex. 5C | Conversion Ex. 5C |
|---|---|---|---|---|---|---|
| 0 | 0 | 0 | 0 | 0 | 0 | 0 |
| Stage 1, after 5 h | 100.4 | 50.2% | 81.8 | 40.9% | 74.5 | 37.3% |
| Stage 2, after 16 h | 142 | 71% | 127 | 63.5% | 117.2 | 58.6% |
| Stage 3, after 5 h | 165.5 | 82.8% | 154.9 | 77.5% | 152.4 | 76.2% |

Example 6

Hydrolysis of Short-chain Conjugated Linoleic Acid Ethyl Esters by Multistage Hydrolysis Hydrolysis Test using Process C)

2 Batches each containing 20 g conjugated linoleic acid ethyl ester based on thistle oil and 40 g water were weighed into closed flasks. 200 mg non-immobilized lipase and 1 g immobilized lipase were then added. The batches were treated as described in Example 5. 200 mg fresh non-immobilized enzyme was added in each hydrolysis stage. The following enzymes were used:

6A) 200 mg Lipomod 34 (*Candida cylindracea* lipase) per stage
6B) 1 g Novozym 435 (*Chromobacterium viscosum* lipase) per stage The conversion of the reaction in the individual stages was determined via the acid value. An acid value of 200 corresponded to a 100% conversion, The results are set out in Table 7.

TABLE 7

Conversion in mutistage hydrolysis

| Reaction time [h] | Acid value Example 6A | Conversion [%] Example 6A | Acid value Example 6B | Conversion [%] Example 6B |
|---|---|---|---|---|
| 0 | 0 | 0 | 0 | 0 |
| Stage 1, after 5 h | 56.6 | 28.3 | 101.9 | 51 |
| Stage 2, after 16 h | 83.9 | 42 | 123 | 61.5 |
| Stage 3, after 5 h | 122 | 61 | 143 | 71.5 |

What is claimed is:

1. A process comprising:
   (a) subjecting a conjugated linoleic acid lower alkyl ester to hydrolysis in the presence of an enzyme to form a hydrolyzate comprising a conjugated linoleic acid and a lower alkanol, wherein at least a portion of the lower alkanol is continuously removed;
   (b) separating the hydrolyzate into an organic phase and an aqueous/alcoholic phase; and
   (c) separating the conjugated linoleic acid from the organic phase.

2. The process according to claim 1, wherein the conjugated linoleic acid corresponds to the general formula (I):

$$R^1CO\text{---}OR^2 \quad (I)$$

wherein $R^1CO$ represents a linoleic acid acyl group having conjugated double bonds and $R^2$ represents an alkyl group having from 1 to 4 carbons.

3. The process according to claim 1, wherein the enzyme comprises a compound selected from the group consisting of esterases, lipases and mixtures thereof.

4. The process according to claim 1, wherein the enzyme comprises at least one microorganism selected from the group consisting of *Alcaligenes.*, *Aspergillus niger*, *Candida antarctica* A, *Candida antarctica* B, *Candida cylindracea*, *Chromobacterium viscosum*, *Rhizomucor miehei*, *Penicilium camemberti*, *Penicilium roqueforti*, *Porcine pancreas*, *Pseudomonas cepacia*, *Pseudomonas fluorescens*, *Rhizopus javanicus*, *Rhizopus oryzae*, and *Thermoinyces lanugenosus*.

5. The process according to claim 2, wherein the enzyme comprises at least one microorganism selected from the group consisting of *Alcaligenes.*, *Aspergillus niger*, *Candida antarctica* A, *Candida antarctica* B, *Candida cylindracea*, *Chromobacterium viscosum*, *Rhizomucor miehei*, *Penicilium camemberti*, *Penicilium roqueforti*, *Porcine pancreas*, *Pseudomonas cepacia*, *Pseudomonas flucrescens*, *Rhizopus javanicus*, *Rhizopus oryzae*, and *Thermomyces lanugenosus*.

6. The process according to claim 1, wherein the enzyme comprises at least one microorganism selected from the group consisting of *Candida antarctica* B, *Chromobacterium viscosum*, and *Thermomyces lanugenosus*.

7. The process according to claim 2, wherein the enzyme comprises at least one microorganism selected from the group consisting of *Candida antarctica* B, *Chromobacterium viscosum*, and *Thermomyces lanugenosus*.

8. The process according to claim 1, wherein the hydrolysis is carried out at a temperature of from 20 to 80° C.

9. The process according to claim 2, wherein the hydrolysis is carried out at a temperature of from 20 to 80° C.

10. The process according to claim 6, wherein the hydrolysis is carried out at a temperature of from 20 to 80° C.

11. The process according to claim 7, wherein the hydrolysis is carried out at a temperature of from 20 to 80° C.

12. The process according to claim 1, wherein the hydrolysis is carried out to a conversion of 60% by weight.

13. The process according to claim 1, wherein a constant water content of from 30 to 70% by weight is maintained during the hydrolysis and at least a portion of the water/lower alkanol phase is continuously removed by application of a vacuum of from 20 to 60±5 mbar.

14. The process according to claim 1, wherein water content is adjusted to from 0 to 20% by weight during the hydrolysis and at least a portion of the water/lower alkanol phase is continuously removed by application of a vacuum of from 20 to 60±5 mbar.

15. The process according to claim 1, wherein the hydrolysis is carried out in two or more stages and a water content of from 50 to 75% by weight is used in each stage.

16. The process according to claim 1, wherein the hydrolysis is carried out to a conversion of greater than 90% by weight.

17. The process according to claim 1, wherein the hydrolysis is carried out to a conversion of greater than 99% by weight.

* * * * *